United States Patent [19]
Willey

[11] Patent Number: 5,345,494
[45] Date of Patent: Sep. 6, 1994

[54] SUPPORT ASSEMBLY FOR RADIOLOGY OR X-RAY MARKERS

[76] Inventor: Walter L. Willey, 8444 Eastwood Ave., Youngstown, Fla. 32466

[21] Appl. No.: 82,543

[22] Filed: Jun. 28, 1993

[51] Int. Cl.[5] .............................................. H05G 1/28
[52] U.S. Cl. ..................................... 378/162; 378/165
[58] Field of Search ............... 378/162, 165, 164, 210, 378/205, 165; 24/3 M, 3 K, 13; 40/665, 636

[56] References Cited

U.S. PATENT DOCUMENTS

| | | | |
|---|---|---|---|
| 3,810,566 | 5/1974 | Adams et al. | 40/104.18 |
| 4,194,122 | 3/1980 | Mitchell et al. | 378/165 |
| 4,625,862 | 12/1986 | Clayton | 24/92 |
| 4,928,298 | 5/1990 | Tanaka | 378/165 |
| 5,092,018 | 3/1992 | Seron | 24/3 B |
| 5,193,106 | 3/1993 | DeSena | 378/163 |
| 5,232,452 | 8/1993 | Russell et al. | 378/163 |

Primary Examiner—David P. Porta
Assistant Examiner—Don Wong
Attorney, Agent, or Firm—Donald A. Kettlestrings

[57] ABSTRACT

A support assembly for conveniently carrying radiology or X-ray markers includes a flexible cord forming a loop with a support element connected to the cord. First and second radiology or X-ray marker elements each are provided with adhesive for enabling the marker elements to be removably attached to the support element, whereby the loop can be positioned around a user's neck to provide quick and easy access to the marker elements.

9 Claims, 2 Drawing Sheets

SUPPORT ASSEMBLY FOR RADIOLOGY OR X-RAY MARKERS

BACKGROUND OF THE INVENTION

This invention relates to a support assembly and more particularly to a support assembly for radiology or X-ray markers.

Radiology or X-ray markers are used many times during each work day by radiology or X-ray technicians. The markers are simply lead letters encased in plastic. One marker is provided with the letter "R" and the other marker is provided with the letter "L". The initials of the technician's name are also provided in lead within each marker. The lead letters are typically encased in a colored transparent plastic so that the letters are visible, and it is conventional practice for the left marker to be colored blue and for the right marker to be colored red.

The purpose of the markers is to indicate on developed X-ray film the left or right side of the body or body extremity, such as a hand or foot. The initials within each marker identify the technician who performed the X-ray exam. The markers are placed next to the body part being examined and exposed to the X-rays, and the developed X-ray film will indicate the letter "R" or "L".

The radiology or X-ray markers used by X-ray technicians are frequently lost or misplaced. To avoid losing the markers, technicians frequently tape the markers to a small piece of discarded X-ray film, and the markers taped to the film are kept in the pants pockets or lab coat pockets of the technician. When needed, the markers are removed from the discarded X-ray film and are retaped to the side of the X-ray cassette (which contains the X-ray film) for the examination.

Taping of markers to discarded X-ray film has not proved to be an effective means for storing or accessing the markers. Pants and lab coats are laundered and the markers taped to discarded X-ray film and left in the pockets of pants or lab coats which are laundered are often lost or are not available when needed. Markers frequently have to be retaped every few days with new adhesive tape to securely hold the markers against the discarded X-ray film. Also, as the adhesive tape becomes less effective over time and as a result of usage, the markers will frequently not properly adhere to the X-ray cassette during the examination. Markers are frequently lost so that the purchase of new markers is often necessary.

It is, therefore, an object of the present invention to provide a support assembly for conveniently storing and transporting radiology or X-ray markers.

Another object is to provide such a support assembly which enables an X-ray technician to quickly and easily gain access to the markers.

Additional objects and advantages of the invention will be set forth in part in the description which follows, and in part will be obvious from the description, or may be learned by practice of the invention. The objects and advantages are realized and attained by means of the instrumentalities and combinations particularly pointed out in the appended claims.

SUMMARY OF THE INVENTION

To achieve these and other objects, the present invention provides a support assembly for radiology or X-ray markers, the assembly comprising: a flexible cord forming a loop; a support element defining first and second surfaces, the support element connected to the cord; a first radiology marker element; first adhesive means attached to the first marker element for enabling the first marker element to be removably attached to the first surface; a second radiology marker element; and second adhesive means attached to the second marker element for enabling the second marker element to be removably attached to the second surface, whereby the loop can be positioned around a technician's neck to provide quick and easy access to the marker elements.

It is to be understood that both the foregoing general description and the following detailed description are exemplary and explanatory but are not restrictive of the invention.

BRIEF DESCRIPTION OF THE DRAWINGS

The accompanying drawings, which are incorporated in and constitute a part of this specification, illustrate an example of a preferred embodiment of the invention and, together with the description, serve to explain the principles of the invention.

DESCRIPTION OF THE PREFERRED EMBODIMENT

Figure 1:
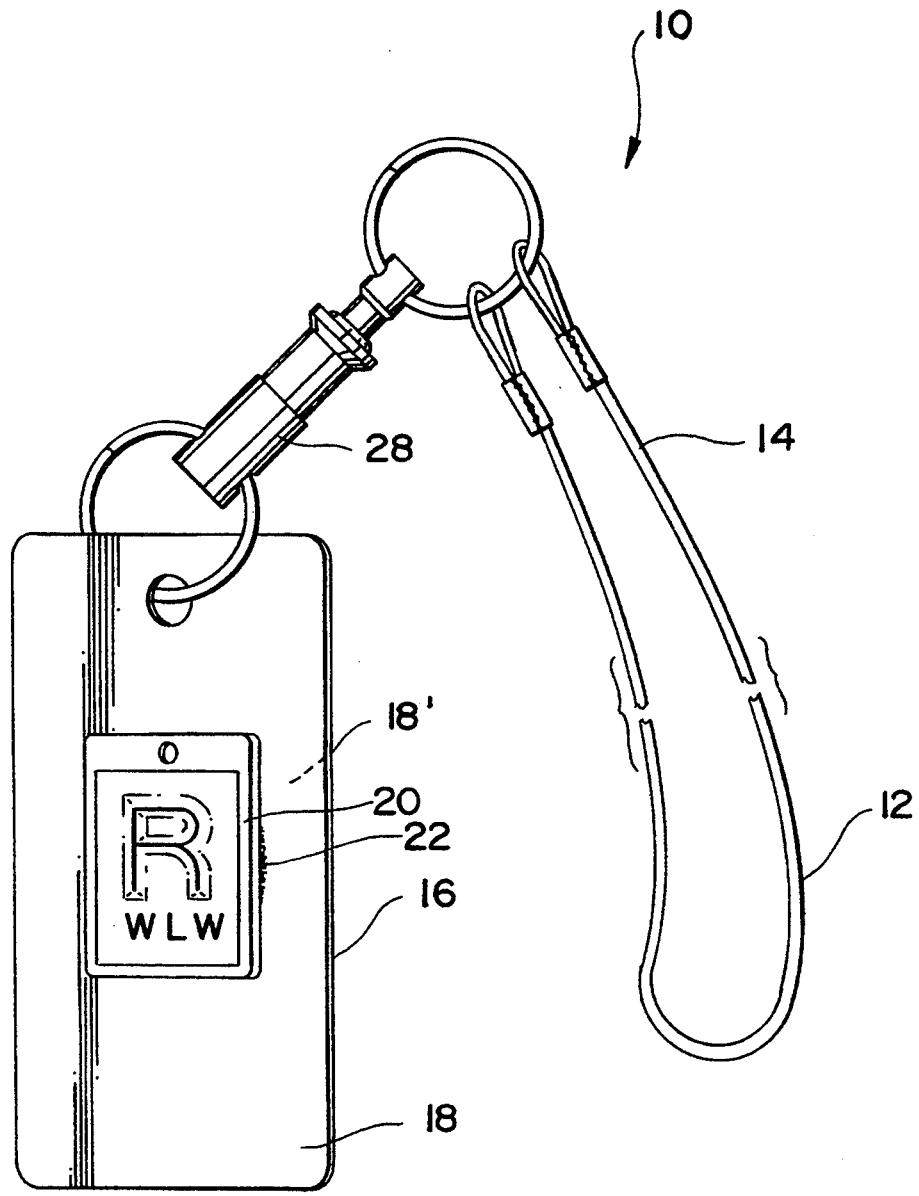
FIG. 1 is a fragmentary perspective view of the support assembly.
Figure 2:
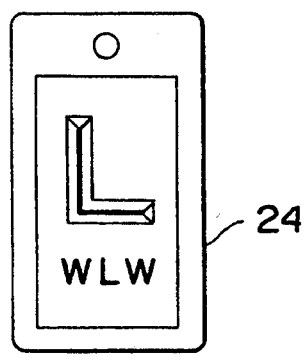
FIG. 2 is a front elevation view showing a marker element.
Figure 3:
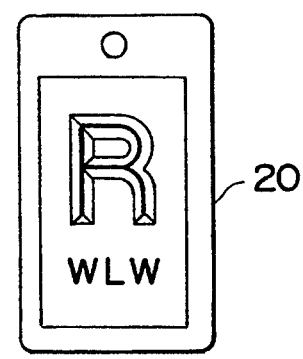
FIG. 3 is a front elevation view showing another marker element.
Figure 4:
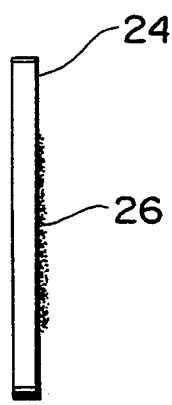
FIG. 4 is a side elevation view showing the marker element of FIG. 2.
Figure 5:
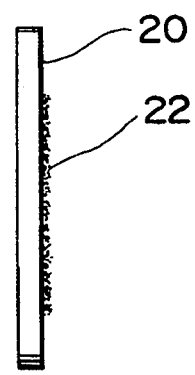
FIG. 5 is a side elevation view showing the marker element of FIG 3.

With reference now to the drawings, wherein like reference characters designate like or corresponding parts throughout the several views, there is shown a support assembly 10 for radiology or X-ray markers which includes a flexible cord 12 forming a loop 14. A support element 16 defines first and second surfaces 18, 18', and support element 16 is connected to cord 12.

A first radiology or X-ray marker element 20 is provided, and first adhesive means 22 are attached to first marker element 20 for enabling marker element 20 to be removably attached to first surface 18 of support element 16.

A second radiology or X-ray marker element 24 is also provided, and second adhesive means 26 are attached to second marker element 24 for enabling marker element 24 to be removably attached to second surface 18' of support element 16.

Support element 16 is preferably a substantially planar plate element, and surfaces 18, 18' are preferably opposed surfaces of the planar plate element.

First surface 18 is preferably red in color and second surface 18' is preferably blue in color. A portion of first marker element 20 is preferably red in color, and a portion of second marker element 24 is preferably blue in color.

First marker element 20 includes the letter "R" and second marker element 24 includes the letter "L". Each of the letters "R" and "L" are comprised of lead, and each of the letters "R" and "L" are preferably encased in transparent plastic material.

Each of marker elements 20, 24 also preferably further includes lead letters of initials of the name of the user or technician to whom the marker elements are assigned.

In accordance with the invention, assembly 10 may include connecting means 28 attached to cord 12 and to support element 16 for removably connecting support element 16 to cord 12. Connecting means 28 is preferably a conventional swivel connector which is separable to permit quick and easy removal of support element 16 from cord 12.

Adhesive means 22, 26 may be any conventional reusable adhesive. One example of such an adhesive is a reusable adhesive sold under the trademark name of Handi-Tak. This product is manufactured by Super Glue Corporation in Hollis, N.Y. It should be understood, however, that any other type of conventionally known reusable adhesive can be used.

In operation and use, cord 12 is typically positioned around the X-ray technician's neck. Marker elements 20, 24 are removably attached to opposed surfaces 18, 18' of support element 16. Marker element 20 is preferably releasably attached to first surface 18 and marker element 24 is preferably releasably attached to second surface 18' of support 16.

Adhesive means 22, 26 are reusable adhesives which are soft and pliable and which provide superior adhesive qualities with repeated use.

As marker elements 20, 24 are needed, the marker elements can be quickly and easily removed from support element 16. After use of marker elements 20, 24, they can be quickly and easily reattached to support element 16.

The invention in its broader aspects is not limited to the specific details shown and described, and departures may be made from such details without departing from the principles of the invention and without sacrificing its chief advantages.

What is claimed is:

1. A support assembly for radiology markers, said assembly comprising:

a flexible cord forming a loop;

a support element defining first and second surfaces, said support element connected to said cord;

a first radiology marker element;

a first adhesive attached to said first marker element removably attaching said first marker element to said first surface;

a second radiology marker element;

a second adhesive attached to said second marker element removably attaching said second marker element to said second surface;

at least a portion of said first surface and at least a portion of said first marker element are of a first predetermined color; and at least a portion of said second surface and at least a portion of said second marker element are of a second predetermined color, whereby said loop is positioned around a user's neck to provide quick and easy access to said marker elements.

2. An assembly as in claim 1 wherein said support element includes a substantially planar plate element.

3. An assembly as in claim 2 wherein said first and second surfaces are opposed surfaces of said plate element.

4. An assembly as in claim 1 wherein said first marker element includes the letter "R" and wherein said second marker element includes the letter "L".

5. An assembly as in claim 4 wherein said letters "R" and "L" are comprised of lead.

6. An assembly as in claim 5 wherein said letters "R" and "L" are encased in plastic.

7. An assembly as in claim 6 wherein each of said marker elements further include lead letters of initials of the name of user or technician to whom said marker elements are assigned.

8. An assembly as in claims 7 wherein said first color is red and wherein said second color is blue.

9. An assembly as in claim 8 further including connecting means attached to said cord and to said support element for removably connecting said support element to said cord.

* * * * *